United States Patent [19]

Brunner

[11] 3,993,691

[45] Nov. 23, 1976

[54] PROCESS FOR SEPARATION OF MONOCARBOXYLIC ACIDS FROM A MIXTURE OF MONOCARBOXYLIC, HYDROXYCARBOXYLIC AND DICARBOXYLIC ACIDS

[76] Inventor: Josef Klemens Brunner, Scheuchzerstrasse 47, Zurich, Switzerland

[22] Filed: Oct. 21, 1974

[21] Appl. No.: 516,658

[30] Foreign Application Priority Data
Oct. 22, 1973   Austria .............................. 8911/73

[52] U.S. Cl. ........................ 260/535 R; 260/533 C; 260/533 N; 260/537 P; 260/538
[51] Int. Cl.² .......................................... C07C 59/04
[58] Field of Search ......... 260/484 R, 535 R, 533 C

[56] References Cited
UNITED STATES PATENTS

| | | | |
|---|---|---|---|
| 2,904,584 | 9/1959 | Payne.............................. | 260/484 R |
| 3,515,751 | 6/1970 | Oberster .......................... | 260/535 R |

*Primary Examiner*—Paul J. Killos
*Attorney, Agent, or Firm*—William R. Woodward

[57] ABSTRACT

In a process for producing esters of carboxylic acids from the waste salt solutions derived from the manufacture of cyclohexanone, the mixture of organic acids obtained by acidulation with a strong acid and separation of an inorganic salt solution is refined to separate the monocarboxylic acids from the hydroxycarboxylic and dicarboxylic acids by a three-stage distillation at a temperature lower than 120° C. The first stage is performed at a moderate vacuum, the second stage at a higher vacuum and the third stage is a steam distillation stage at a moderate vacuum, with the steam requirements reduced by returning to the evaporator an aqueous phase that is readily separated from the distillate. The use of steam in this manner only in the third stage reduces the steam requirements to economic proportions. More than 99% of the monocarboxylic acids may be separated from the other carboxylic acids in this fashion.

2 Claims, No Drawings

PROCESS FOR SEPARATION OF MONOCARBOXYLIC ACIDS FROM A MIXTURE OF MONOCARBOXYLIC, HYDROXYCARBOXYLIC AND DICARBOXYLIC ACIDS

This invention relates to an improved method of separating monocarboxylic organic acids from dicarboxylic and hydroxy acids which facilitates the obtaining of useful esters of organic acids from the waste salt solution produced in the manufacture of cyclohexanone. As explained in an earlier filed patent application, Ser. No. 372,021, of the present inventor jointly with Hellmuth Schindlbauer and Walter Eichberger, now U.S. Pat. No. 3,859,335, such esters are obtainable by separation of an aqueous and an organic phase by acidulating the waste salt solution with a strong acid, followed by distilling off an aqueous fraction at temperatures below 120° C and, thereafter, esterifying with a lower alcohol.

In the manufacture of cyclohexanone by catalytic oxidation of cyclohexane with oxygen, a reaction mixture results that contains, in addition to the desired product, larger quantities of various saturated monocarboxylic and dicarboxylic acids. Before further treatment of the reaction mixture, the acids are treated with water and/or alkali solutions so that they are obtained in the form of a concentrated aqueous solution of their salts. Such solutions constitute an undesired and inconvenient by-product of the production of cyclohexane. They contain, more or less, the following quantities of carboxylic acids in the form of their sodium salts:

| ACID | % BY WEIGHT |
| --- | --- |
| Formic | 1.0 |
| Acetic & propionic | 0.5 |
| Butyric | 1.5 |
| Valeric | 7.5 |
| Caproic | 1.75 |
| Hydroxycaproic | 5.25 |
| Oxalic | 1.25 |
| Succinic | 0.75 |
| Glutaric | 1.75 |
| Adipic | 4.75 |

Along with these there are also contained small quantities of other organic materials, particularly also resins.

There has been no lack of experiments to do something with these solutions, because considerable costs are involved in their destruction or other disposition. Japanese Pat. No. 68 17 163 describes a process in which these solutions are first acidulated with mineral acids to a pH value of 0.7 to 3, after which the two resulting phases are separated and the organic phase is extracted with a halogenated hydrocarbon. The extract is freed of the solvent by evaporation and the remainder is then separated into the individual monocarboxylic acids by fractionation. This process cannot operate economically, since out of 3,000 kg of waste salt solution, with addition of 400 kg of sulphuric acid, only 130 kg of monocarboxylic acids can be obtained.

A better suggestion is made in Polish patent 54 750, where the waste salt solution is described as being neutralized to a pH value of 5 with sulphuric acid and then cooled to 18° C. Two phases are produced, of which the upper organic phase is separated and distilled with steam. This distillate also divides into two phases, of which the upper organic phase is then fractionated. Valeric and caproic acids are obtained as products. Here, also, there is the disadvantage that with a relatively high expense only two materials are obtained as products and the others not only are lost in the materials contained in the waste salt solution, but cause additional costs for the necessary destruction of the waste material.

A substantial advance is the treatment described in the above-mentioned U.S. Pat. No. 3,859,335. In that treatment, the waste salt solution is first acidulated with a strong acid, thus setting free the carboxylic acids. Two phases are produced, a concentrated sodium sulphate solution and a water-containing mixture of carboxylic acid that is then given further treatment. The carboxylic acids still in solution are removed from the sodium sulphate solution by an extraction and thus recovered. The carboxylic acid mixture is separated by distillation into a distillate containing the water and the volatile monocarboxylic acids and a residue remaining as a mother liquor containing the dicarboxylic acids and hydroxycarboxylic acids. The monocarboxylic acids are esterified with isobutanol and the dicarboxylic and hydroxycarboxylic acids with methanol. The esters of the monocarboxylic acids, as well as those of the dicarboxylic and hydroxycarboxylic acids, can be used as solvents.

The above-described process constitutes a genuine advance, because in this way it is possible to convert the waste salt solution practically fully into salable products. As the result of the larger quantity of salable products, it is possible not only to obtain greater monetary proceeds, but also to save the costs of an otherwise necessary waste disposal installation for the other products.

In carrying out the process of the aforesaid prior application, however, difficulties still remain in the separation of the monocarboxylic acids, because it is not possible to remove the monocarboxylic acids from the mixture with the dicarboxylic and hydroxycarboxylic acids completely by mere heating, so that larger quantities, particularly of caproic acid, always remained in the mother liquor. The purity of the esters produced in the next step was therefore impaired and, besides, a part of the valuable caproic acid was lost. If the suggestion given in the aforesaid Polish Pat. No. 54,750 is followed, i.e. if a steam distallation is used for separation, the necessary steam requirement is very high, amounting to 8 to 14 times the quantity of the monocarboxylic acids to be distilled in order to obtain a complete separation. This high quantity of steam results in costs that are so high that the process is uneconomic.

SUBJECT MATTER OF THE PRESENT INVENTION

Briefly, it has been surprisingly discovered that, on the one hand, a complete separation of the monocarboxylic acids from the dicarboxylic and hydroxycarboxylic acids can be obtained and, on the other hand, an economic but still effective use of steam can be made, if the distillative separation of the monocarboxylic acids is carried out in three stages, in the first separating water under a moderate vacuum, in the second separating the bulk of the monocarboxylic acids by heating in a higher vacuum and in the third separating the remainder of the monocarboxylic acids with the addition of steam under a moderate vacuum.

In the first stage the aqueous mixture of the monocarboxylic acids is heated in a vacuum high enough for the vapors, predominantly water vapor, to be condensed by indirect heat exchange at the temperature of the available cooling water. For the normally usual cooling water temperatures of 15° to 35° C, this means a pressure of 0.1 to 0.3 atm. The use of directly operating spray coolers is not possible in this case, because the vapors, in addition to water, still contain a certain proportion of low-boiling monocarboxylic acids that would otherwise be lost.

In the second stage the mixture is heated under as good a vacuum as possible, thus at a pressure of about 0.002 to 0.02 atm., in order to remove the monocarboxylic acids to as great an extent as possible. As the result of their higher boiling points, these acids also, in spite of the higher vacuum, can be condensed by indirect cooling with cooling water. In the mother liquor of the evaporator there remains still about 2 to 8% of monocarboxylic acids, predominantly n-caproic acid. Heating of the remaining material to a higher temperature than 120° C, however, leads to polymerization of the hydroxy acids therein contained and is, therefore, not permissible.

In the third stage of distillation a pressure such as that used in the first stage is again used and the material is heated to a temperature of 80°to 120° C, but under addition of steam it is thus possible to remove almost completely the remaining monocarboxylic acid content from the mother liquor, the final content of monocarboxylic acid of the latter lying in any case below 1%. The vapors drawn off are condensed by indirect cooling with cooling water and they divide into two liquid phases. Whereas the upper organic phase is drawn off as products, the lower phase, consisting predominantly of water, is put back into the vaporizer of the distilling apparatus. A direct addition of steam in the vaporizer is inappropriate since larger amounts of waste water would then come off, containing only small but still interfering quantities of monocarboxylic acid, so that a separate washing to remove them would be necessary. Moreover, with too much water resulting from continuous addition of steam, this quantity of monocarboxylic acids carried off in waste water would be lost.

In the manner above described, it is possible to separate the monocarboxylic acids practically completely from the mixture of carboxylic acids at costs that do not make the products obtained abinitio uneconomic. Whereas in the process according to Polish Pat. No. 54 750 for each ton of monocarboxylic acid recovered, some 8 to 14 tons of steam must be supplied, in the process of the present invention only 1 to 3 tons of steam need be supplied. Since the corresponding amounts of heat must also be removed, there results likewise an equivalent saving in the quantity of necessary cooling water.

EXAMPLE 10 kg of by-product solution as available from the production of cyclohexanone from cyclohexan by the oxidation with air and containing (besides other substances):

| formic acid | 100 g |
|---|---|
| acetic and propionic acid | 50 g |
| butyric acid | 150 g |
| valeric acid | 750 g |
| caproic acid | 175 g |
| 6-hydroxicaproic acid | 525 g |
| oxalic acid | 125 g |
| succinic acid | 75 g |
| glutaric acid | 175 g |
| adipic acid | 475 g | in the form of the respective sodium salt are filled into a 15 lt - round bottom flask. Within 40 minutes 1,85 kg of 95 % - sulfuric acid are added under vigorous stirring. After the end of the addition of the sulfuric acid the temperature of the mixture is 63° C. The mixture is then filled into a separation funnel and allowed to stand for 8 minutes. During this time two layers are formed, the lower one being a solution of sodium sulfate in water, the upper one a mixture of various organic compounds and about 20 % of water. The sodium sulfate solution is separated and discarded. The organic phase (3 kg) is transferred into a distillation equipment, brought under a vacuum of about 150 mm of mercury and heated to 65° C. The vapours are condensed in a Liebig-type cooler supplied with cooling water of 23° C, the condensate (690 g) is predominantly water.

After changing the condensate receiver the vacuum is brought to 12 mm of mercury and the mixture is slowly heated to 90° C. The condensate (790 g) is collected, it consists predominantly of fatty acids of $C_3$ to $C_5$.

The condensate receiver is again changed and the distillation flask is connected with a vapourizer containing the aqueous layer from a previous distillation. Vacuum of 100 mm of mercury is applied, the vapourizer is heated to boiling and the distillation flask to 90° C. The condensate in the collector separates into two layers, the lower one being predominantly water, the upper one valeric and capronic acid (300 g). The lower phase (1000 g) is used for filling the vapourizer for another run.

I claim:

1. In a process for producing useful materials from the waste solution of salts of monocarboxylic acids having 1 to 6 carbon atoms, dicarboxylic and hydroxycarboxylic acids produced in the manufacture of cyclohexanone by the catalytic oxidation of cyclohexane in which said waste salt solution is acidulated with sulfuric acid to produce an aqueous phase which is a concentrated sulfate salt solution and an organic phase and a water-containing mixture of monocarboxylic, hydroxycarboxylic and dicarboxylic acids which phases are thereafter separated, the improved method of distillatively separating the monocarboxylic acids from the water-containing mixture of monocarboxylic, hydroxycarboxylic and dicarboxylic acids of the aforesaid organic phase which comprises the steps of:

subjecting said mixture to a first distillation stage at a temperature below 120° C and at a pressure in the range of 0.1 to 0.3 atm., to obtain a first fraction;
   subjecting the remaining mixture to a second distillation stage at a temperature under 120° C at a pressure in the range of 0.002 to 0.02 atm. to obtain a second fraction, and
   subjecting the remaining mixture to a third distillation stage at a temperature below 120° C at a pressure in the range of 0.1 to 0.3 atm. with the addition of steam, to obtain a third fraction,
   whereby said first, second and third fractions include monocarboxylic acids.

2. A method as defined in claim 1 in which in said third distillation stage, the third fraction forms a lighter organic phase and a heavier aqueous phase, and the said aqueous phase is separated from said organic phase and returned to the mixture under distillation to supply steam required for the distillation.

* * * * *